United States Patent
Demos et al.

(10) Patent No.: US 7,257,437 B2
(45) Date of Patent: Aug. 14, 2007

(54) AUTOFLUORESCENCE DETECTION AND IMAGING OF BLADDER CANCER REALIZED THROUGH A CYSTOSCOPE

(75) Inventors: Stavros G. Demos, Livermore, CA (US); Ralph W. deVere White, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 902 days.

(21) Appl. No.: 10/400,024

(22) Filed: Mar. 25, 2003

(65) Prior Publication Data
US 2004/0006276 A1 Jan. 8, 2004

Related U.S. Application Data

(63) Continuation-in-part of application No. 10/190,231, filed on Jul. 5, 2002, now Pat. No. 7,016,717.

(51) Int. Cl.
A61B 6/00 (2006.01)
G02F 1/01 (2006.01)
(52) U.S. Cl. ...................... 600/473; 250/330
(58) Field of Classification Search ............... 600/473, 600/407, 474, 475, 476; 250/330, 331, 332, 250/333, 334
See application file for complete search history.

(56) References Cited

U.S. PATENT DOCUMENTS

| | | | |
|---|---|---|---|
| 3,817,633 A * | 6/1974 | White ..................... 356/323 |
| 4,930,516 A | 6/1990 | Alfano et al. |
| 4,957,114 A | 9/1990 | Zeng et al. |
| 5,042,494 A | 8/1991 | Alfano |
| 5,131,398 A | 7/1992 | Alfano et al. |
| 5,261,410 A | 11/1993 | Alfano et al. |
| 5,348,018 A | 9/1994 | Alfano et al. |
| 5,467,767 A | 11/1995 | Alfano et al. |
| 5,593,879 A * | 1/1997 | Steller et al. ............... 435/325 |
| 5,769,081 A | 6/1998 | Alfano et al. |
| 5,847,394 A | 12/1998 | Alfano et al. |
| 6,169,289 B1 * | 1/2001 | White et al. ............. 250/458.1 |
| 6,269,169 B1 * | 7/2001 | Funk et al. ................. 382/100 |
| 6,413,267 B1 * | 7/2002 | Dumoulin-White et al. .. 607/89 |
| 6,687,000 B1 * | 2/2004 | White ......................... 356/328 |
| 6,975,898 B2 * | 12/2005 | Seibel ......................... 600/473 |
| 6,975,899 B2 * | 12/2005 | Faupel et al. ............... 600/476 |
| 7,016,717 B2 * | 3/2006 | Demos et al. .............. 600/473 |

OTHER PUBLICATIONS

Udagawa, M., et al., "Aberrant Porphyrin Metabolism in Hepatocellular Carcinoma," Biochemical Medicine 31, pp. 131-139, Academic Press, Inc. (1984).

Pitts, J., et al., "Autofluorescence characteristics of immortalized and carcinogen-transformed human bronchial epithelial cells," Journal of Biomedical Optics 6(1), pp. 31-40 (Jan. 2001).

(Continued)

*Primary Examiner*—Daniel Robinson
(74) *Attorney, Agent, or Firm*—Michael C. Staggs; John H. Lee (57) ABSTRACT

Near infrared imaging using elastic light scattering and tissue autofluorescence and utilizing interior examination techniques and equipment are explored for medical applications. The approach involves imaging using cross-polarized elastic light scattering and/or tissue autofluorescence in the Near Infra-Red (NIR) coupled with image processing and inter-image operations to differentiate human tissue components.

13 Claims, 6 Drawing Sheets

OTHER PUBLICATIONS

Zawirska, B., "Comparative Porphyrin Content in Tumors with Contiguous Non-Neoplastic Tissues," Neoplasma 26, 2, pp. 223-229 (1979).

Malik, Z., et al., "Destruction of erythoroleukaemic cells by photoactivation of endogenous porphyrins," Health Sciences Research Center, Dept. of Life Sciences, Bar-Ilan University, Ramat-Gan 52100, Israel, 7 pages, (Mar. 9, 1987).

Zhang, G, et al., "Far-red and NIR Spectral Wing Emission from Tissues under 532 and 632 nm Photo-excitation," Lasers in the Life Sciences, vol. 9, pp. 1-16, (1999).

Alfano, R., et al., "Laser Induced Fluorescence Spectroscopy from Native Cancerous and Normal Tissue," IEEE Journal of Qantum Electronics, vol. QE-20, No. 12, pp. 1507-1511 (Dec. 1984).

Navone, N., et al, "Porphyrin biosynthesis in human breast cancer. Preliminary mimetic in vitro studies," Med. Sci. Res., 16, pp. 61-62, (1988).

Richards-Kortum, R., et al., "Spectroscopic Diagnosis of Colonic Dysplasia," Photochemistry and Photobiology, vol. 53, No. 6, pp. 777-786, (1991).

Demos, S., et al., "Subsurface Imaging Using the Spectral Polarization Difference Technique and NIR Illumination," Lawrence Livermore National Laboratory, UCRL-JC-131091 Preprint, 7 pages (Jan. 23, 1999).

Demos, S., et al., "Tissue imaging for cancer detection using NIR autofluorescence," Lawrence Livermore National Laboratory, 8 pages, (May 2002).

Schomacker, K., et al., "Ultraviolet Laser-Induced Fluorescence of Colonic Tissue: Basic Biology and Diagnostic Potential," Lasers in Surgery and Medicine, 12, pp. 63-78, (1992).

* cited by examiner

AUTOFLUORESCENCE DETECTION AND IMAGING OF BLADDER CANCER REALIZED THROUGH A CYSTOSCOPE

RELATED APPLICATION

This application is a Continuation-In-Part of application Ser. No. 10/190,231 filed Jul. 5, 2002 now U.S. Pat. No. 7, 016, 717, and claims priority thereto.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a medical diagnostic for the examination of tissue components. Specifically, the present invention relates to an optical imaging method and apparatus for in-vivo and real-time imaging of bladder cancer and determination of tumor margins.

2. Description of Related Art

Diagnostic medical equipment typically includes time-consuming, bulky, expensive apparatus that often exposes human tissue components to potentially harmful radiation and or chemicals. Optical methods and systems for the identification of objects that possess different optical properties or abnormal compositions embedded in scattering media such as, human tissue, are desirable because such systems can be designed as compact, inexpensive, portable, and non-invasive spectral investigative tools. Optical spectroscopy, as one such optical method example, has been widely used to acquire fundamental knowledge about physical, chemical, and biological processes that occur in biomaterials. Most tissue spectroscopy research has employed UV to visible light sources from 250-nm to 600-nm. The main active fluorophores in this spectral region are tryptophan, collagen, elastin, NAD(P)H, flavins and prophyrins. The disadvantage of these wavelengths is their short photon penetration depth in tissues, which leads to extraction of information only from superficial tissue layers.

Accordingly, a need exists for optical diagnostic methods and systems to be utilized in a compact portable system to recover optical information with regard to human tissue and organ compositions.

SUMMARY OF THE INVENTION

Accordingly, the present invention provides a diagnostic apparatus that includes: at least one electromagnetic radiation source, an arranged interior examination device adapted to transmit the radiation source and further adapted to relay a near-infrared scattered and/or an autofluorescence emission radiation, and a detector adapted to capture the scattered and/or near-infrared emission radiation produced by the radiation sources and optically coupled to the interior examination device so that characterization of the one or more tissue components is capable of being performed.

Another aspect of the present invention provides a diagnostic apparatus that includes: at least two substantially narrow-band electromagnetic radiation wavelength sources for simultaneous illumination of one or more tissue components, an arranged interior examination device adapted to transmit the wavelength sources for illumination of the tissue components and further adapted to relay a near-infrared scattered radiation of the illuminated tissue components; and a detector adapted to simultaneously capture one or more images produced by the near-infrared scattered radiation from the tissue components so that characterization of the one or more tissue components is capable of being performed.

Another aspect of the present invention provides a diagnostic apparatus that includes: one or more laser sources, a cystoscope adapted to transmit laser source emission and further adapted to relay a near-infrared scattered electromagnetic and/or a near infrared autofluorescence emission radiation; and an on-chip charge CCD adapted to capture the scattered and/or near-infrared emission produced by the laser sources, wherein a computer configured with an image processing software can characterize the captured near-infrared scattered and/or near-infrared autofluorescence emission radiation from the tissue components.

Another aspect of the present invention provides a diagnostic apparatus that includes: at least two laser sources for simultaneous illumination of one or more tissue components, a cystoscope adapted to transmit laser source illumination and further adapted to relay near-infrared scattered radiation; and a two-dimensional CCD adapted to simultaneously capture the scattered emission produced by the laser sources so that a computer configured with an image processing software can characterize the captured near-infrared scattered radiation from the tissue components.

Still another aspect of the present invention is directed to an improved diagnostic imaging method for medical applications comprising the steps of: interrogating one or more tissue components with an interior examination device capable of directing one or more substantially narrow band electromagnetic radiation sources to provide illumination of one or more tissue components and further capable of relaying a near infrared scattered and/or a near infrared autofluorescence emission radiation from the illuminated tissue components, detecting a scattered electromagnetic radiation and/or a near infrared autofluorescence emission from the tissue components; and characterizing the detected scattered electromagnetic radiation and/or autofluorescence emission from said tissue components.

Accordingly, the present tissue imaging system and method provides a portable, cost effective, non-invasive arrangement, capable of directing substantially monochromatic electromagnetic radiation and capable of providing spectrally processed images in the much desired need for differentiating components in human and/or animal tissues.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring now to the drawings, specific embodiments of the invention are shown. The detailed description of the specific embodiments, together with the general description of the invention, serves to explain the principles of the invention.

Unless otherwise indicated, all numbers expressing quantities of ingredients, constituents, reaction conditions and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

General Description

The present invention combines monochromatic laser sources, a broadband light source, optical filtering, a computer, optical imaging, and computer software capable of image analysis that includes inter-image operations. A useful feature of the present invention is that fresh surgical resections collected from patients may be measured in-vitro (e.g., in an artificial environment) and in-vivo (e.g., during medical biopsy or intervention procedures) immediately upon collection. In addition, the system has particular utility as a tissue component interrogation tool for human tissue specimens, such as, but not limited to, kidney, uterine, bladder, breast, liver, adipose, abnormal (i.e., contrary to normal structure), normal, and veins and/or nerves from surrounding muscle tissue.

Accordingly, the present invention provides a non-invasive optical analysis means suitable for rapid, in-vitro or in-vivo differentiation of human tissue components.

Specific Description

Figure 1:
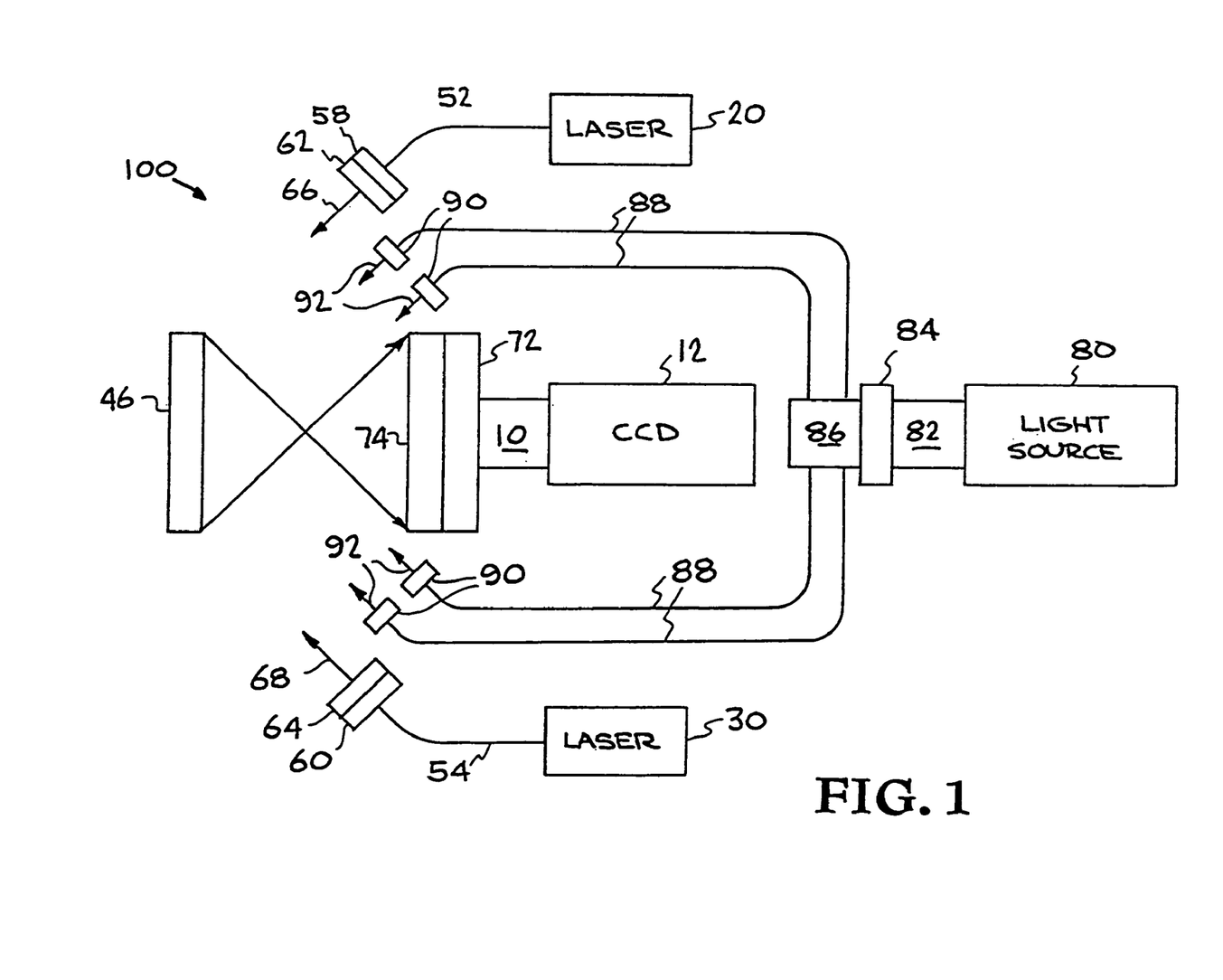
FIG. 1 is a simplified diagram of an exemplary medical tissue imaging apparatus incorporating elastic light scattering, fluorescence imaging, and image processing capabilities.

Turning now to the drawings, a diagram that illustrates exemplary embodiments of a system constructed in accordance with the present invention is shown in FIG. 1. The system, designated generally by the reference numeral 100, provides a method and apparatus for interrogating and characterizing human tissue components in a clinical environment from a specimen. System 100, as shown in FIG. 1, designed as a portable, compact apparatus, includes the following basic components: a CPU with software for sample image processing (not shown); a lens system 10 for image collection; an image acquisition system 12; a substantially monochromatic 20 light source; an optical band-pass filters 62; an optical polarization filters 58; a sample holder (not shown); a white light source 80; and the remaining components (discussed below).

The sample image processing software (not shown) can be a commercially available product. However, any image analysis software capable of performing image processing with inter-image operations may be employed with the present invention to provide tissue component differentiation.

Lens system 10, for example a camera lens, is coupled to image acquisition system 12, such as, but not limited to, a liquid nitrogen cooled CCD camera, a two-dimensional array detector, an avalanche CCD photodetector, a photomultiplier or a photodiode capable of point by point scanning. However, any imaging device constructed to the design output parameters for image acquisition system 12 can also be employed in the present invention. Such exemplary image acquisition systems 12 capable of performing time-integrated images may be employed with the present invention to image illuminated tissue sample 46 housed in a kinematically (i.e., can be removed and rapidly repositioned with accuracy) mounted sample holder (not shown).

Monochromatic light sources 20 is a low power laser having an output power of at least 1 mW that operates at 632 nm. However, any laser source capable of providing a wavelength and intensity capable of differentiating tissue components may be employed with the present invention. White light source 80 provides a broadband of wavelengths for the scattering experiments. White light source 80 and monochromatic light source 20 are brought into the imaging compartment (not shown) by an optical means such as, a plurality of large core optical fibers 52, and 88 (i.e., multi-mode fibers).

Monochromatic light source 20 is used for photoexcitation to provide NIR autofluorescence images, including a polarizer 58 and a narrow band-pass filter 62 positioned to ensure a predetermined narrow band of electromagnetic radiation with a predetermined polarization orientation to uniformly illuminate sample 46. White light source 80, to provide elastic light scattered images, additionally has one or more polarization filters 90 positioned to orient one or more illumination output beams 92 to a predetermined polarization orientation prior to uniformly illuminating a tissue specimen.

Sample 46 is illuminated with a set of one or more images, preferably seven, recorded for each sample. The objective is to employ hyperspectral (i.e., using various spectroscopic techniques and multiple wavelength and/or spectral bands) imaging to investigate the ability of polarized light in combination with native NIR tissue autofluorescence to image and differentiate human tissue components. An exemplary useful benefit of the present invention is to image and differentiate human tissue components, such as, but not limited to, cancerous growth from contiguous normal tissue or nerves and/or vascular structures from muscle.

The combined investigative approach method embodiment of polarized light scattering with NIR native tissue autofluorescence under long-wavelength laser excitation to reveal optical fingerprint characteristics for tissue components can be initiated by either of the following two methods of the present invention.

Autofluorescence

A related method for using autofluorescence emission (i.e., the spectral wing emission greater than 600 nm) to detect cancerous tissue is disclosed in Incorporated by reference Co-pending, Co-filed U.S. application Ser. No. xxx,xxx titled "Method And Apparatus For Examining A Tissue Using The Spectral Wing Emission therefrom Induced By Visible To Infrared Photoexcitation" by Alfano et al., the disclosure is herein incorporated by reference in its entirety. NIR autofluorescence, as disclosed in the above referenced co-pending U.S. application, is particularly useful for monitoring and/or imaging the porphyrin content in tissues. Porphyrins, effective at transferring electrons in sub-cellular organelles known as mitochondria are known to fluoresce in the visible light portion of the luminescence spectra. In addition, there is strong evidence that the heme-biosynthetic pathway, and therefore the production of porphyrins is disturbed in any new and abnormal growth, such as, cancer tissue. Thus, NIR autofluorescence of fluorophores, such as, but not limited to, porphyrins, provides one such exemplary medical diagnostic means of enhancing the contrast between normal and cancerous tissue components. However, the present invention provides a useful improvement thereof by incorporating autofluorescence images, image processing coupled with inter-image manipulations with elastic light scattering images discussed below to produce high contrast, high visibility images capable of differentiating substantially various human tissue components from a specimen, such as, but not limited to, normal and tumor tissue.

Turning again to FIG. 1, system 100 includes monochromatic light source 20 that transmits laser light through optical fiber 52. As one embodiment, monochromatic light source 20 may include a Helium-neon laser that operates at about 633 nm. However, any monochromatic laser light source operating at wavelengths from about 250 nm to about 1100 nm can be employed to provide NIR autofluorescence emission images for the present invention. Light source 20 is selected by a remote control pad (not shown) and directed by optical fiber 52 into an imaging compartment (not shown). Narrow-band filter 58 having an optical band-pass of at least 10 nm, and polarizer, 62 capable of producing linear, circular or elliptical polarization are positioned at the distal end of optical fiber 52 to ensure a degree of polarized monochromatic light beam 66 received from light source 20. The output of optical fiber 52 is constructed to provide beam 66 with a diverging property to substantially uniformly illuminate sample 46.

FIG. 1 also shows an alternate embodiment that includes monochromatic light source 30, such as, an Nd:YAG diode-pumped solid-state laser that operates at 532 nm, to transmit laser light through optical fiber 54. Light source 30 is selected by the remote control pad (not shown) and directed by optical fiber 54 into the imaging compartment (not shown). Narrow-band filter 60 having an optical band-pass of at least 10 nm, and polarizer, 64 capable of producing linear, circular or elliptical polarization are positioned at the distal end of optical fiber 54 to ensure a degree of polarized monochromatic light beam 68 received from light source 30. The output of optical fiber 54 is constructed to provide beam 68 with a diverging property to substantially uniformly illuminate sample 46.

Autofluorescence emission is generated from light sources 20, or 30, and then collected from tissue sample 46 in a back-scattering geometry, as generally shown by optical rays 94, by lens system 10 having one or more interchangeable camera lenses, preferably a 50-mm focal length camera lens. An analyzing polarizer 74 is positioned before lens system 10 on a translation stage such that parallel linear polarization, orthogonal cross-polarization, orthogonal elliptical polarization, same elliptical polarization, opposite circular polarization, or non-polarization analysis of the autofluorescence emission may be employed. A bandpass filter 72 is additionally positioned before lens system 10 to ensure a proper spectral band selection between about 650 nm and about 1500 nm for imaging. The autofluorescence emission is time gated for 0.1 or more seconds and recorded by image acquisition system 12, preferably a Princeton Instrument Model No. TE/CCD-512 liquid nitrogen cooled camera. The output of image acquisition system 12 is coupled to a computer (not shown), e.g., a laptop computer, and image processed by commercially available image processing software, such as, Roper Scientific Winspec/32 and/or Winview/32 software, and displayed on, for example, a computer screen for human eye diagnosis or for image software analysis.

Elastic Light Scattering

The NIR polarized elastic light scattering method of the present invention to delineate differences in absorption and scattering in human tissue components allows an end-user to acquire clinical diagnostic deep-subsurface (e.g., at least 1 cm) images. An illumination wavelength, preferably greater than 500 nm from an electromagnetic radiation source is utilized to provide mean photon penetration depth larger than 1 mm. Linear cross-polarization and spectral analysis of the scattered photons substantially removes the photon information from the orthogonal illumination polarization resulting from the surface and allows substantially all of the scattered photons from the subsurface tissue to be imaged.

In addition, a spectral polarization difference technique (SPDI) and NIR illumination related method embodiment is utilized in the present invention and is disclosed in incorporated by reference, U.S. application Ser. No. 5,847,394, titled "Imaging of objects based upon the polarization or depolarization of light," by Alfano et al., the disclosure which is herein incorporated by reference in its entirety. With SPDI, different illumination wavelengths are utilized to record images having a differential mean photon penetration depth. Thus, a smaller differential in the illumination wavelengths provides narrower differential depth zones while a larger difference in two exemplary illuminating wavelengths gives rise to a wider depth zone. Cross-polarization and normalization analysis coupled with inter-image operations, such as, but not limited to, subtraction between one or more illuminating wavelengths provide information as to the tissue structure between the penetration depths of the one or more respective probe illumination wavelengths. However, the present invention provides a useful improvement thereof, as similarly discussed herein before, by incorporating inter-image operations of autofluorescence images and light scattering, such as, single wavelength cross-polarized light scattered images, to provide higher visibility and contrast information from images for humans tissue component differentiation.

Accordingly, the present invention utilizes NIR autofluorescence, NIR light scattering, inter-image operations between individual methods, (preferably inter-image operations incorporating both autofluorescence and light scattering), to provide differential tissue component information within one or more exemplary images.

Turning again to FIG. 1, a broad-band, i.e., its electromagnetic spectrum covers the visible, (e.g., 0.4 μm to 0.7 μm), and a substantial amount of the invisible, (e.g., 0.7 μm to 2.0 μm), white light source 80 is selected by the remote pad (not shown) to transmit up to 100 watts of white light to coupled optical fiber bundle 82. Fiber bundle 82 has its distal end coupled to a tunable filter (not shown) or a filter wheel 84 that is remotely controlled by a filter wheel remote pad (not shown) for insertion of a predetermined optical filter (not shown). Such a predetermined narrow-band (e.g., 40 nm) interference filter in the visible or invisible between about 700-nm and about 1000-nm spectral range can thus be rapidly positioned at the output distal end of fiber bundle 82. However, any type of band-pass filter means, for example broad spectral band filters or long-pass interference filters can be employed in practice of the invention.

A manifold 86 is coupled to an optical delivery means, such as, one or more large core optical fibers 88, preferably four. Manifold 86 is additionally coupled to filter wheel 84 to receive and direct the selected wavelength band through optical fibers 88 in order to substantially uniformly illuminate sample 46. One or more linear polarizers 90 are constructed at the output of one or more optical fibers 88 to ensure a degree of linear polarization of one or more scattering diverging illumination output beams 92 having predetermined selected wavelength bands.

The elastically scattered light is then collected from tissue sample 46 in a back-scattering geometry, as generally shown by optical rays 94, by lens system 10 similar to the autofluorescence measurements discussed above. Analyzing polarizer 74 is positioned on a translation stage such that parallel polarization, cross-polarization or non-polarization analysis of the elastic light scattering may be employed. Image acquisition system 12 is time gated for 0.1 or more seconds and one or more images as a result of the elastic light scattering from the sample is recorded. The output of image acquisition system 12 is coupled to a computer (not shown), e.g., a laptop computer, image processed, and displayed on, for example, one or more computer screens for human eye diagnosis or for image software analysis as previously discussed.

An exemplary prototype was constructed and positioned in a lab space located at the UC Davis Medical Center in Sacramento, Calif. The following autofluorescence emission and elastic light scattering images illustrating adipose, cancerous and contiguous normal human tissue, obtained from fresh surgical resections from more than 60 patients are used to only illustrate some of the novel imaging capabilities of the present invention.

Figure 2A:
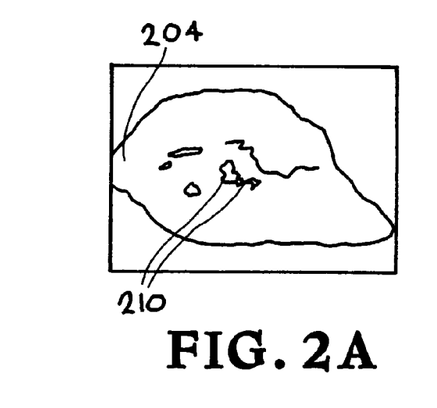
FIG. 2 shows a series of breast tissue images collected by the present invention.
Figure 2B:
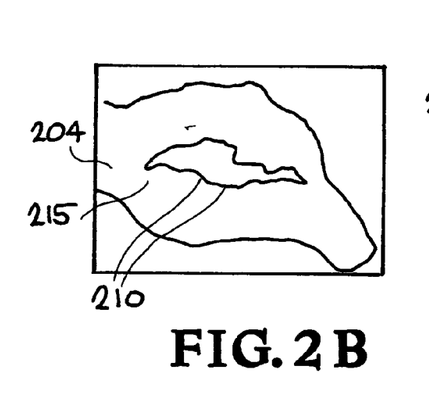
Figure 2C:
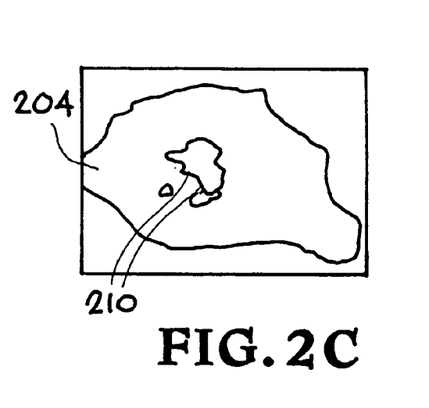
Figure 2D:
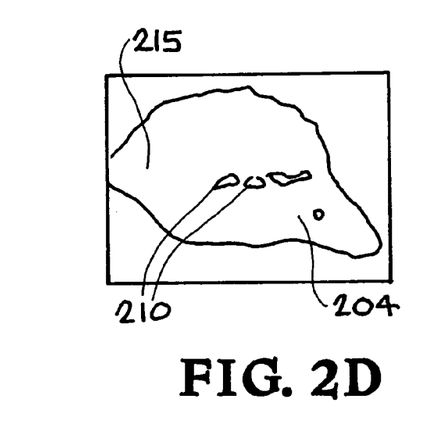
Figure 2E:
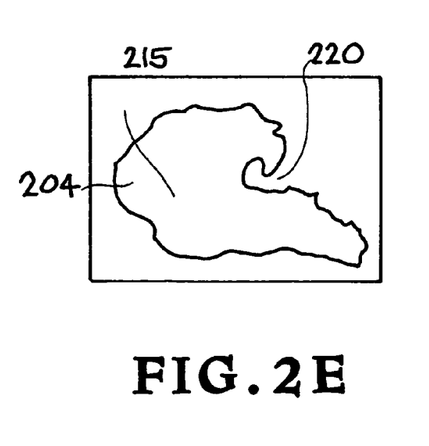
Figure 2F:
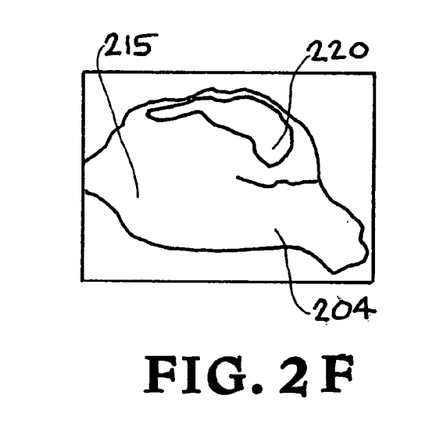

FIG. 2 illustrates a capability of the present invention with a set of images of an approximately 4-cm×3-cm human breast tissue specimen 204 with multifocal high grade ductal carcinoma 210 shown in FIG. 2d, surrounded by fibrous supporting tissue 215 with an adjacent area of fatty 220 (i.e., adipose) infiltration as shown in FIG. 2f. FIGS. 2a and 2b show autofluorescence images in the 700-nm and 1000-nm spectral region under a 532-nm and a 633-nm substantially monochromatic illumination, respectively. FIG. 2c shows a light scattering image of specimen 204 under 700-nm illumination. FIG. 2d shows a novel feature of the present invention wherein a ratio of the autofluorescence image of FIG. 2b, divided by the light scattering image of FIG. 2c, improves visibility and contrast of a pair of higher emission 1-mm diameter ductal carcinoma lesions 210 as determined by histopathological (i.e., microscopic tissue disease) assessment (i.e., hematoxylin-eosin stain). In addition, the ratio image provides better delineation of the tumor margins. This effect is also demonstrated in the examples shown in succeeding FIGS. 3 through 5. Furthermore, FIG. 2e shows an inter-image ratio of a cross-polarized light scattering 1000 nm band-pass image (not shown) divided by the cross-polarized light scattering 700 nm band-pass image of FIG. 2c. FIG. 2f shows an inter-image ratio of cross-polarized light scattering 700 nm band-pass image of FIG. 2c divided by the autofluorescence image after 532 nm illumination of FIG. 2a.

From the images of the specimen shown in FIG. 2, only the NIR fluorescence image under 632.8-nm excitation FIG. 2b and the ratio image of FIG. 2d show a correlation with the assessment of lesions 210. The integrated NIR emission intensity arising from these cancerous parts of the sample is higher than surrounding tissue 215 of FIGS. 2b, 2d, and 2f, by a factor of about 1.5 in FIG. 2b and a factor of about 1.6 in FIG. 2d, FIG. 2e and FIG. 2f show the presence of adipose tissue 220 with a higher average intensity of adipose tissue component 220 compared to the surrounding connective tissue 215 of FIG. 2e and FIG. 2f of about 0.25 and 2.5 for the image shown in FIG. 2e and FIG. 2f, respectively. The ratio images of FIG. 2d and FIG. 2f reveal high contrast and increased visibility of different tissue components (i.e., lesions 210 of FIG. 2d and adipose 220 tissue of FIG. 2f, respectively) while subjecting specimen 204 to different illumination wavelengths and by different inter-image operations. Thus, the present invention can be advantageous in increasing the visibility of various tissue components in a specimen by varying system parameters (i.e., illumination wavelength, spectral band-pass region, inter-image operations, etc.).

FIGS. 3 shows a set of images obtained from two liver specimens. FIG. 3a, 3b, and 3c, show a histologic section of a specimen 206, taken from a benign growth as determined by clinical assessment. FIGS. 3d, 3e, and 3f, show a histologic section of a specimen 208 of a well-circumscribed 0.8×0.5-cm nodule. The histologic features of the nodule, as determined by clinical assessment, are those of a hepatoblastoma (i.e., a tumor of the liver). FIGS. 3a and 3d are NIR autofluorescence images recorded under 632-nm illumination, respectively. FIGS. 3b and 3e are NIR cross-polarized light scattering images recorded under 700-nm illumination respectively. FIGS. 3c and 3f are the resultant ratio images of the autofluorescence images FIGS. 3a and 3d over light scattering images 3b and 3e, respectively. Benign tumor 310 is visible in specimen 206 of image 3c. The digitized intensity in the area of the benign tumor 310 is higher between about 0.20 when compared to that of the adjacent normal liver tissue 315. However, organ composition, depth of tissue components, and illumination and inter-image operations, may vary the digitized intensity information so as to best visualize specific tissue components.

Figure 3A:
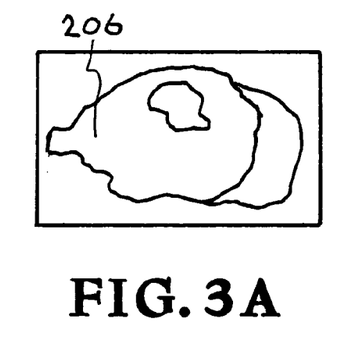
FIG. 3 shows a series of malignant and benign tumor images from a liver specimen collected by the present invention.
Figure 3B:
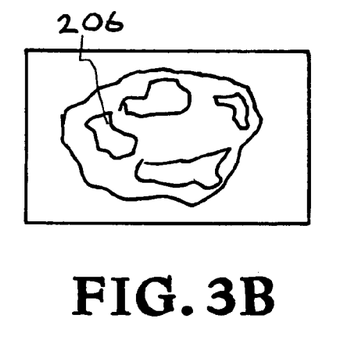
Figure 3C:
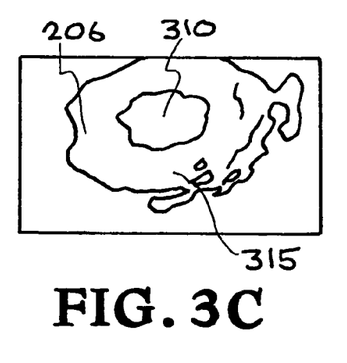
Figure 3D:
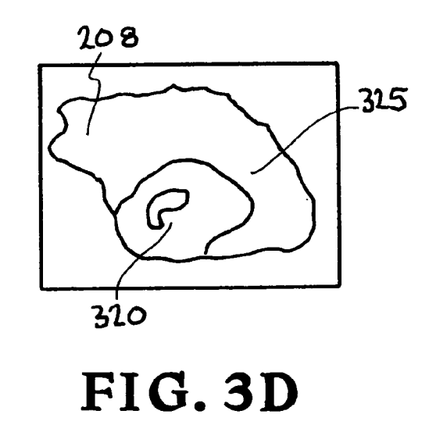
Figure 3E:
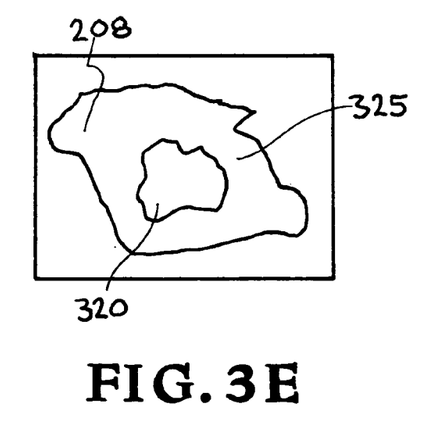
Figure 3F:
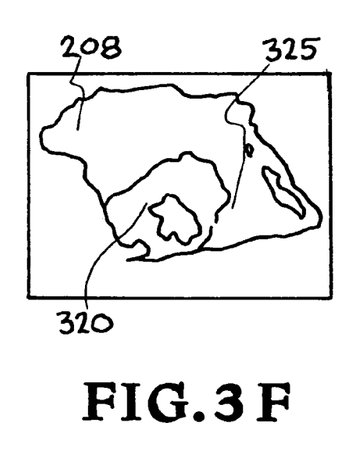

It is noted however, that cancer nodule 320, in specimen 208 of FIGS. 3d, 3e, and 3f, is shown as an even brighter in intensity feature with respect to a surrounding normal tissue 325. More specifically, this intensity difference between tissue components 320, and adjacent normal tissue 325 is further increased in NIR autofluorescence image FIG. 3d under 632.8-nm excitation by a factor of about 0.65. In FIG. 3e (cross-polarized light scattering image under 700-nm illumination) the digitized intensity in the area of the cancer nodule 320 is higher by a factor of about 0.15 when compared to that of the adjacent normal liver tissue 325. However, the highest contrast accompanied by best visualization of tissue margins of cancer nodule 320 is in the ratio image shown in FIG. 3f, wherein an overall intensity difference between cancer nodule 320 and adjacent normal tissue 325 is a factor of up to about 0.90.

Figure 4A:
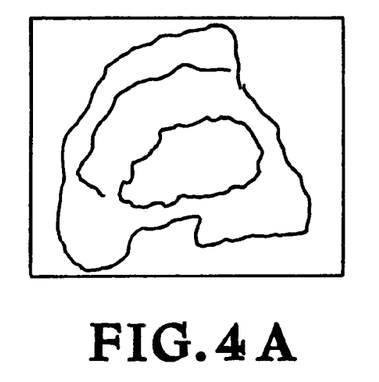
FIG. 4 shows a series of uterine images collected by the present invention.
Figure 4B:
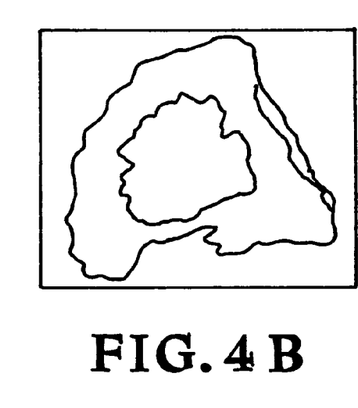
Figure 4C:
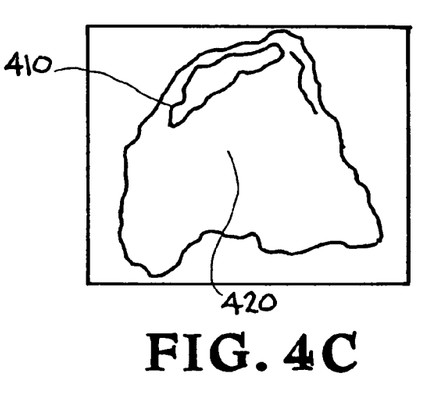
Figure 5A:
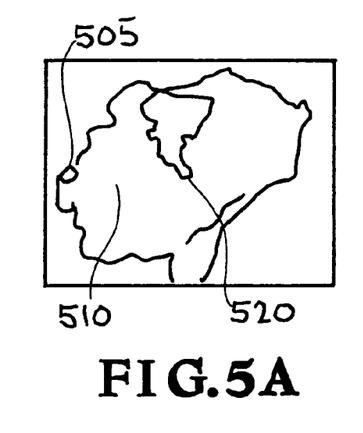
FIG. 5 shows a series of bladder images collected by the present invention.
Figure 5B:
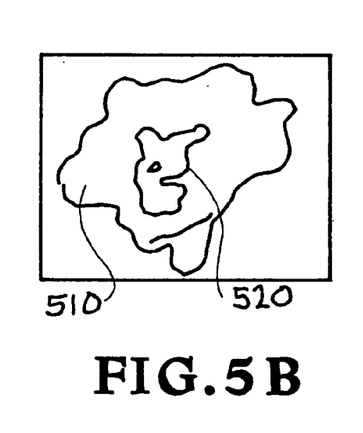

FIGS. 4a, 4b, and 4c, and FIGS. 5a-g show images of the method of the present invention in delineating cancerous uterine and bladder tissue from adjacent normal tissue, respectively. FIGS. 4a and 5a show NIR autofluorescence images of the uterine and bladder organs under 632-nm illumination respectively while FIGS. 4b and 5b show NIR cross-polarized images of the respective organs under 700-nm illumination. For the uterine specimen, FIG. 4c (i.e., the ratio of NIR cross-polarized image under 700-nm illumination of FIG. 4b over NIR autofluorescence image under 632-nm illumination of FIG. 4a), shows a contrast ratio that clearly differentiates cancerous uterine tissue 410 from surrounding tissue, including normal tissue 420. Specifically, FIG. 4c shows a contrast ratio of digitized counts of cancerous tissue 410 from adjacent normal tissue 420 by a factor of at least 0.65. However, as discussed herein before, tissue depth, composition, etc., results in different contrast ratios but with the same qualitative visual assessment.

Figure 5C:
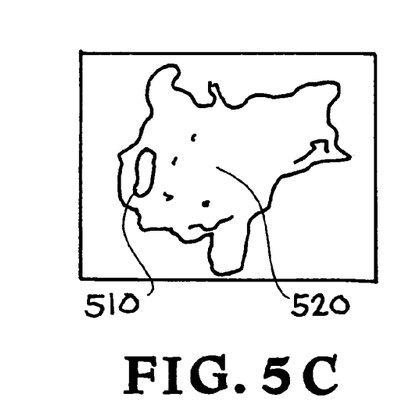

FIG. 5c (i.e., the ratio of NIR cross-polarized image under 700-nm illumination FIG. 5b over NIR autofluorescence image under 632-nm illumination FIG. 5a) shows a high visibility, high contrast bladder cancerous tissue 510 from surrounding normal bladder tissue 520 similar to the case for uterine tissue shown in FIG. 4. FIG. 5a shows necrotic tissue 505 (cells that have died as a result of cancerous growth) as a high intensity region. Moreover, FIG. 5a (NIR autofluorescence image under 632-nm illumination) and FIG. 5b (NIR cross-polarized image under 700-nm illumination) also show cancerous tissue 510 as a dark feature that is about 0.40 less in digitized intensity with respect to the surrounding lighter featured normal bladder tissue 520. However, better contrast and better visibility is still the image shown in FIG. 5c as compared in FIG. 5a and FIG. 5b separately.

Figure 5D:
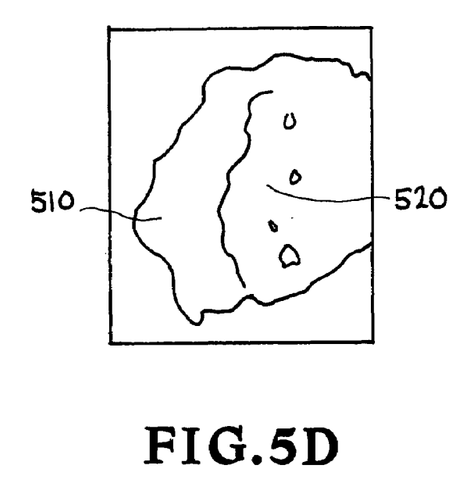
Figure 5E:
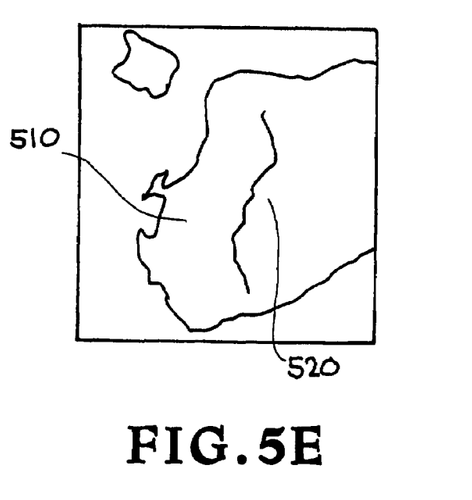
Figure 5F:
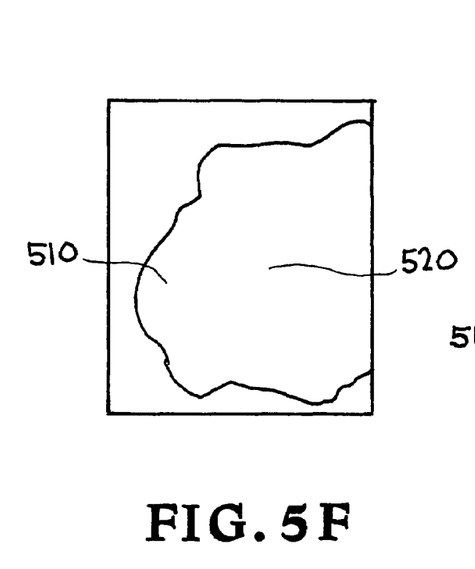
Figure 5G:
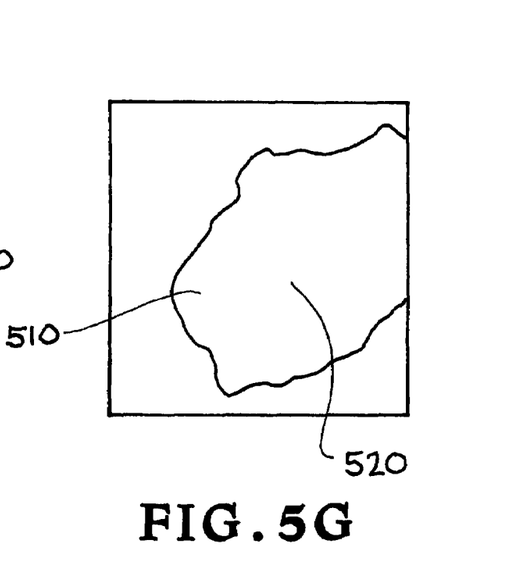

FIG. 5d shows an example of a near-infrared fluorescence image under 532-nm illumination with the cancerous tissue 510 and the normal bladder tissue 520 areas denoted with the associated arrows. FIG. 5e shows a ratio image following division of the NIR autofluorescence image obtained under 633-nm excitation as shown in FIG. 5a over that obtained under 532-nm excitation as shown in FIG. 5d. In this case, cancerous tissue 510 has a digitized intensity that is higher by a factor of about 0.82 compared to that arising from normal bladder tissue 520. FIG. 5f shows a ratio image obtained from division of the 700-nm cross-polarized light scattering image, as shown in FIG. 5a, by the NIR autofluorescence image under 532-nm excitation as shown in FIG. 5b, whereby cancerous tissue 510 has a higher digitized intensity by a factor of about 1.1 compared to normal bladder tissue 520. Therefore array of images shown in FIGS. 5a-f clearly indicate that cancerous tissue 510 can be visualized and tumor margins (e.g., the area separating normal bladder tissue 520) clearly delineated. Autofluorescence images can help detect and image cancer that is located in the superficial tissue layers between about 1 and about 2 mm from the surface. The SPDI technique however can reveal the presence of different tissue components greater than about 2 mm provided that there is difference in the light scattering characteristics between the tissue components, namely cancer and normal tissue. The ratio image shown in FIG. 5g, (obtained by division of the cross-polarized light scattering image under 1000-nm illumination over that obtained under 700-nm illumination) shows very small variations (e.g., less than about 3%) between normal bladder tissue 520 and cancerous tissue 510. This indicates that the change in the scattering intensity between normal and cancer tissues remain relatively unchanged as a function of the illumination wavelength. However, the absolute changes between normal and cancer tissue may be somewhat different between specimens from different patients due to various factors, such as, but not limited to, differences in fluorescence and scattering arising from tissues from different patients or tissue specimens having both normal and cancer components in close proximity.

The present invention thus combines advantageous methods for tissue component differentiation. The first method examines polarized light scattering spectral imaging. The images attained using elastic light scattering delineate differences in absorption and scattering between tissue components.

Another advantageous method of the present invention involves imaging of various tissue types using the NIR emitted light under, for example, 632.8-nm and 532-nm excitation. The images attained using this method are useful for monitoring and/or imaging endogenous fluorescing agents, such as, porphyrins, which is useful for the detection of neoplastic (i.e., diseased) tissue formation. In addition, NIR autofluorescence is further enhanced by utilizing excitation at different wavelengths. For example the 1-mm tumor lesions in the breast specimen depicted in FIG. 2c are visible in the NIR autofluorescence images under 632.8-nm excitation but not under 532-nm excitation. Therefore, different illumination wavelengths provided by the present invention can provide insight into different fluorophores that are indicative of neoplastic human or animal tissue. Moreover, inter-mage operations of the present invention, such as, but not limited to, light scattering over NIR autofluorescence images, has particular utility for high contrast, high visibility images for tissue component differentiation.

Utilization of Cystoscopes

The most common presenting feature of transitional cell carcinoma (TCC) of the bladder is hematuria, (i.e., a pathological condition in which the urine contains blood). Diagnosis of such a tumor is typically performed by outpatient cystoscopic evaluation (i.e., interior examination of a patient). A patient is as one procedure, subsequently scheduled for a day-care surgery requiring anesthesia, cystoscopic examination, and transurethral resection (TUR). Following this surgery, the patient is discharged home the same day, and tissue is sent for histologic examination. Less than about 75% of such tumors have not invaded the bladder muscle and are called superficial. Initial therapy consists of a TUR.

If it is determined that the tumor is superficial and of low-risk of recurrence and progression, the patient is then followed with cystoscopic examinations in the office about 4 times a year for about 2 years, then about 2 times a year for about 2 subsequent years, then about yearly. Low-risk tumors have been defined as grade I, grade II and stage Ta. If the tumor is regarded as high-risk for tumor recurrence and progression, i.e., all grade III tumors, T1 grade II and III multi-focal tumors, concomitant carcinoma in situ in the bladder (CIS), or tumors that are sessile (i.e., permanently attached) these patients will receive intravesical (i.e., within the bladder) therapy as an outpatient. They will then undergo the same cystoscopic follow-up as outlined above.

TCC tumors may recur after resection because: 1) bladder tumors are multi-focal lesions by nature and subsequent tumors arise from areas of carcinoma in situ in the bladder (CIS), that are not yet visible, 2) the area of the tumor is not fully resected, 3) the urothelium is injured during the resection process and seeding by TCC cells occurs, and/or 4) recurrence represents a new tumor development. Therefore, the embodiment detailed hereinafter provides a benefit in the management of diseases, such as, TCC, to the patient, doctor, and healthcare system.

Figures 6A, 6B:
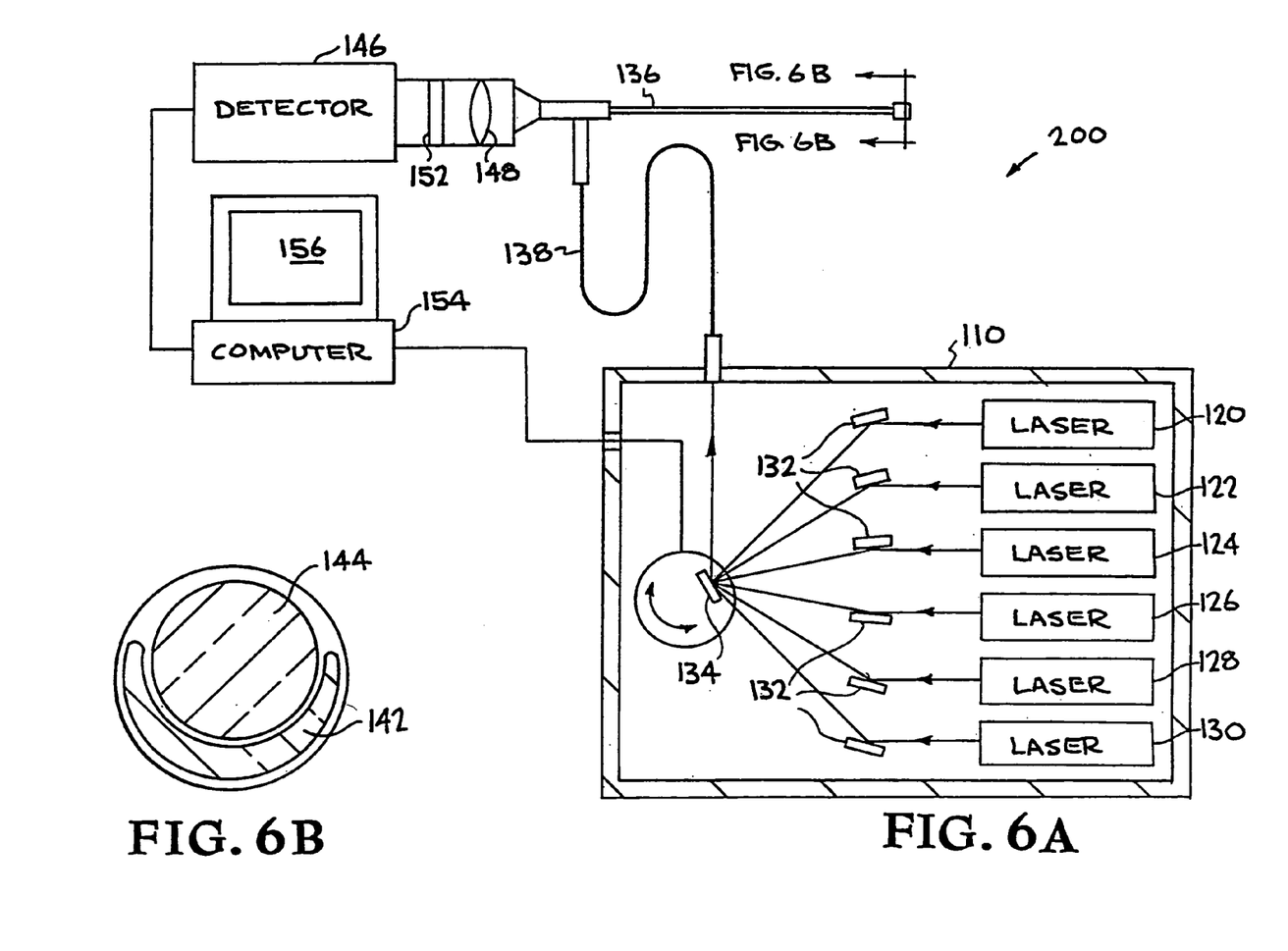
FIG. 6(a) shows a schematic layout of the main components of an example cystoscopic diagnostic system.
FIG. 6(b) shows a cross-sectional view of the output tip of an example cystoscope.

FIG. 6(a) shows an example schematic layout of a high sensitivity unit (HSU) system, capable of collecting NIR autofluorescence images with sufficiently low, (i.e., less than about 1 sec), exposure time, and is generally designated by reference numeral 200. System 200, includes an illumination assembly 110 having at least one, often at least two, and more often, at least six substantially monochromatic CW lasers, 120, 122, 124, 126, 128, 130, such as, but not limited to, diode lasers, frequency doubled and tripled diode lasers, light emitting diodes (LEDs), broadband light sources wherein a substantially monochromatic spectral band is capable of being selected, and/or gas lasers that may be optically directed, by, for example, one or more mirrors 132, to a wavelength selection means 134, such as, but limited to, computer controlled high-speed galvanometer scanner mirrors, optical switches, and/or manual operation. A selected monochromatic laser, such as, for example laser 120, by wavelength selection means 134, is optically coupled to an interior examination device 136, such as, for example, an endoscope or a ureterscope, more often a cystoscope, by an external illumination fiber bundle 138. Illumination from laser 120, is delivered at a point of interest inside a patient's bladder through an illumination output 142, as illustrated in FIG. 6(*b*), of interior examination device 136. An image, (not shown) is formed by a lens 144, as shown in FIG. 6(*b*). Such a lens 144 is configured at the output of interior examination device 136, and is capable of relaying radiation to project an image on an imaging device 146, such as, for example, a liquid nitrogen cooled CCD camera, a two-dimensional array detector, and/or an on-chip amplification CCD camera, as shown in FIG. 6(*a*), via coupling optics 148 and after passing through one or more optical filters 152. The output of imaging device 146 is capable of being characterized by a means, such as, but not limited to, a computer 154 configured with image processing software, e.g., a laptop computer or a personal computer, and/or a human operator, such as, for example, a pathologist. The operator evaluates the tissue components after for example, inter-image operation display by one or more visualization devices 156, to distinguish tissue features deemed important information to his or her trained eye.

In one embodiment, optical filter 152, is arranged to include a 670-nm long-pass filter that allows transmission for image acquisition only of the far-red and NIR photons. For autofluorescence measurements, excitation lasers having a lower wavelength than an example cutoff wavelength (e.g., 670 nm) of filter 152, such as, for example, lasers having illumination wavelengths of 405-nm, 532-nm and/or 632-nm, will therefore pass only the NIR autofluorescence light through such an example filter 152 while scattered light at the excitation wavelengths, e.g., 405-nm, 532-nm and/or 632-nm, will be rejected. For the formation of light scattering images, lasers with longer wavelengths such as, for example, 670-nm, 820-nm and/or 970-nm, operate at higher wavelengths than the cut-off wavelength of an example 670-nm optical filter 152, and as a result, all images will pass through filter 152.

An image, can be captured by imaging device 146, via, for example, an on-chip charge amplification CCD camera, and characterized by a computer configured with image processing software and/or an operator after visualization by display means 156. CCD cameras that are based on on-chip charge multiplication gain technology can have gain factors as high as about 1000×, which allows short exposure times of less than about 1 sec for autofluorescence images. Such a technology allows camera weights of about 1 Kgr to be manageable so that an operator is capable of holding such a camera operatively attached to interior examination device 136, such as, a cystoscope, in a comfortable manner to allow such an operator to remain still while imaging device 146 is capturing an image. Two types of cystoscopes can be adapted into the present invention and are standard equipment at the UC Davis Medical Center located in Sacramento, Calif. One such cystoscope is flexible and is used in the outpatient setting and is based on image preserving fiber bundle technology. A second cystoscope is not flexible and is used during transurethral resection. It is based on image transmission using fiber optic image conduits technology. Each capable cystoscope has an image collection element (i.e., an image preserving fiber bundle or glass rod) and a means to illuminate a sample (e.g., bladder). Illumination is delivered using a fiber bundle that is part of the assembly of the cystoscope. This internal illumination fiber is coupled to an external light source through external illumination fiber bundle 138 that attaches at an input of a cystoscope's internal fiber bundle.

As another example arrangement, when implementing SPDI subsurface imaging, illumination output 142 is arranged with a polarization filter (not shown) either fixedly attached or coupled with a fixture (not shown) capable of being removed for specific applications. A polarization filter (not shown), having a polarization orientation orthogonal with respect to the polarization filter at output 142, is also arranged with coupling optics 148. By such an arrangement, an image is formed by photons that have polarization orientation orthogonal to that of the illumination. Such formed images are then capable of being characterizing by, for example, a computer 154 configured with image processing software and/or an operator after visualization.

As a further arrangement, system 200 is capable of being adapted to operate as a "maximum speed unit" (MSU) system. Such a system 200, provides simultaneous images of a tissue sample (not shown) from at least two, and more often, at least three illumination wavelengths, e.g., 670-nm, 820-nm and, 970-nm. In this embodiment, a second illumination assembly (not shown) is configured to direct one or more wavelengths to tissue components of interest through optically coupled interior examination device 136. Lens 144, as shown in FIG. 6(*b*), can optically relay simultaneous images from the illuminated tissue components for capture by imaging device 146. In addition, lens 144 of interior examination device 136, such as a cystoscope, is capable of being optically coupled to an image preserving fiber bundle (not shown) to also relay simultaneous images to coupling optics 148 for capture by imaging device 146. These spectral image components are spatially separated, such as, for example, by using appropriate spectral dispersion optics (not shown), and/or mirrors before projection onto imaging device 146. In this arrangement, imaging device 146 can include a two-dimensional detector (e.g., a 400×1300 pixels CCD) so that each spectral image component is capable of being simultaneously projected on different parts of imaging device 146. Appropriate software implemented by computer 154 can then perform inter-image operations between image components associated with different illumination wavelengths for characterizing the illuminated tissue components in accordance with the methodology of the SPDI technique.

As an example protocol, an examination of a tissue region may involve acquisition or generation of up to about ten images such as, three cross polarized images under 670-nm (670 CPI), 820-nm (820 CPI) and, 970-nm (970 CPI) illumination, three SDPI images from subtraction following normalization of the cross polarized images under illumination at 970-nm and 670-nm (e.g., 9-7 SPDI), 970-nm and 820-nm (e.g., 9-8 SPDI), 820-nm and 670-nm (e.g., 8-7 SPDI), two NIR autofluorescence images under 532-nm (532 AFI) and 632.8-nm (633 AFI) excitation, an autofluorescence ratio image of 633-nm illumination over 532-nm excitation (AFRI) and a ratio image of light scattering at 700-nm over the autofluorescence image under 532-nm excitation (SARI). An operator evaluates the generated images with four example scenarios shown in Table 1:

TABLE 1

| Feature is visible on image: | | | | | | | | | | |
|---|---|---|---|---|---|---|---|---|---|---|
| 670 CPI | 820 CPI | 970 CPI | 9-7 SPDI | 9-8 SPDI | 8-7 SPDI | 532 AFI | 633 AFI | AFRI | SARI | Evaluation |
| yes | yes | yes | yes | no | yes | yes | yes | yes | yes | Superficial cancer |
| no | no | no | no | yes | yes | no | no | no | no | Subsurface tumor |
| yes | yes | yes | yes | yes | yes | yes | yes | yes | yes | Cancer extends from surface to muscle |
| yes | yes | yes | yes | no | yes | yes | yes | no | yes | Surface lesion, not cancer |

During operation of the system, the operator may start by displaying images in a monitor that will help determine if there is cancer on the surface (i.e. superficial cancer as shown in the last column). If there is no surface cancer, the operator may search for subsurface tumors (i.e., SPDI images). If there is cancer on the surface, the operator may use the SPDI images to evaluate the depth of penetration of the tumor (i.e., the cancer extends from the surface to muscle or the identified tissue is a surface lesion and not cancerous).

Embodiments of system 200, as shown in FIG. 6*a* are beneficial in multiple ways. As some examples, system 200 enhances the follow-up of patients with Ta and T1 tumors, it increases the accuracy of detecting recurrent tumors, Ta lesions could be treated in the office rather than the operating room, and pink areas which can be confused as either CIS or inflammation following intravesical therapy could be accurately analyzed. In addition, system 200 is capable of being implemented on ureteroscopes to diagnose lesions of the ureter and renal pelvis. Finally, there would be a small group of patients in whom system 200 could be adapted for percutaneous, (i.e., through the skin), access to the upper tract.

Accordingly, system 200 provides an enormous benefit to patients, doctors, and the healthcare system in managing and treating disease such as cancer (e.g., TCC).

It should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A diagnostic apparatus, comprising:
   at least two substantially narrow-band electro-magnetic radiation wavelength sources directed to illuminate one or more tissue components,
   an interior examination device adapted to transmit the wavelength sources for illumination of the tissue components and further adapted to relay a near-infrared scattered radiation of the illuminated tissue components,
   a detector adapted to simultaneously capture images produced by the near-infrared scattered radiation from the tissue components; and
   means to characterize the captured near-infrared scattered radiation from the tissue components.

2. The apparatus of claim 1, wherein the detector includes a two-dimensional CCD such that the spectral information produced by the illumination of tissue components by the wavelength sources are capable of being simultaneously projected on different parts of the detector.

3. The apparatus of claim 1, wherein the interior examination device includes a non-flexible cystoscope capable of transurethral resection.

4. The apparatus of claim 1, wherein the interior examination device includes a flexible cystoscope.

5. The apparatus of claim 1, wherein the interior examination device includes a cystoscope adapted to relay an image to the detector with an operatively coupled image preserving optical fiber bundle.

6. The apparatus of claim 1, wherein the characterization means includes a computer and image processing software and/or human interpretation of displayed real time images of tissue component features that are important to a trained operator.

7. The apparatus of claim 6, wherein one or more inter-image operations are performed by the image processing software on the images.

8. The apparatus of claim 7, wherein the inter-image operations include operations on a detected scattered radiation from the source wavelengths and/or polarization states from the tissue components to enhance image contrast and visibility of the tissue components under examination.

9. The apparatus of claim 7, wherein the inter-image operations are between at least two images selected from a near-infrared cross-polarized light scattering image of a first wavelength, a near-infrared cross-polarized light scattering image of a second wavelength, a near-infrared parallel-polarized light scattering image of a first wavelength, a near-infrared parallel-polarized light scattering image of a second wavelength produced by a polarized excitation to enhance image contrast and visibility of one or more tissue components.

10. The apparatus of claim 1, wherein the detector captures an analyzed degree of polarization near-infrared scattered electromagnetic radiation.

11. The apparatus of claim 10, wherein the degree of polarization comprises one or more optical polarizers adapted to polarize the wavelength sources and wherein the analyzed degree of polarization comprises one or more polarizers adapted to analyze the scattered electromagnetic radiation received from the tissue components by the detector.

12. The apparatus of claim 1, wherein the apparatus is capable of imaging and differentiating one or more grades of bladder tumors.

13. A diagnostic apparatus, comprising:
  at least two laser sources directed to illuminate one or more tissue components,
  a cystoscope adapted to transmit the laser sources for illumination of the tissue components and further adapted to relay a scattered near-infrared radiation produced by the illuminated tissue components,
  a two-dimensional CCD, adapted to simultaneously capture images produced by the scattered near-infrared radiation from the tissue components; and
  a computer configured with an image processing software to characterize the captured near-infrared scattered radiation from the tissue components.

* * * * *